United States Patent [19]
Yamamoto et al.

[11] Patent Number: 5,948,427
[45] Date of Patent: Sep. 7, 1999

[54] MICROPARTICULATE SURGICAL ADHESIVE

[75] Inventors: Ronald K. Yamamoto, San Francisco; Robert E. Short, Los Gatos, both of Calif.

[73] Assignee: Point Medical Corporation, San Carlos, Calif.

[21] Appl. No.: 08/639,285

[22] Filed: Apr. 25, 1996

[51] Int. Cl.$^6$ ......................................... A61K 9/50
[52] U.S. Cl. .................. 424/426; 424/463; 424/423; 424/452; 128/898
[58] Field of Search .................... 424/426, 463, 424/423, 452; 128/898

[56] References Cited

U.S. PATENT DOCUMENTS

| | | | |
|---|---|---|---|
| 2,986,477 | 5/1961 | Eichel | 117/122 |
| 3,779,942 | 12/1973 | Bolles | 252/316 |
| 3,875,074 | 4/1975 | Vassiliades et al. | 252/316 |
| 3,886,085 | 5/1975 | Kiritani et al. | 252/316 |
| 4,273,672 | 6/1981 | Vassiliades | 252/316 |
| 4,298,598 | 11/1981 | Schwarz et al. | 424/101 |
| 4,362,566 | 12/1982 | Hinterwaldner | 106/85 |
| 4,377,572 | 3/1983 | Schwarz et al. | 424/101 |
| 4,804,691 | 2/1989 | English et al. | 523/118 |
| 4,900,303 | 2/1990 | Lemelson | 604/54 |
| 4,909,251 | 3/1990 | Seelich | 606/213 |
| 4,940,852 | 7/1990 | Chernack | 523/211 |
| 5,045,569 | 9/1991 | Delgado | 521/60 |
| 5,156,613 | 10/1992 | Sawyer | 606/213 |
| 5,209,776 | 5/1993 | Bass et al. | 106/124 |
| 5,260,071 | 11/1993 | Lemelson | 424/463 |
| 5,277,979 | 1/1994 | Kielbania, Jr. et al. | 428/402.21 |
| 5,487,895 | 1/1996 | Dapper et al. | 424/278.1 |

FOREIGN PATENT DOCUMENTS

| | | | |
|---|---|---|---|
| 0 466 383 A1 | 1/1992 | European Pat. Off. | A61L 25/00 |
| 2 281 861 | 3/1995 | United Kingdom | A61L 15/42 |
| WO 92/13025 | 8/1992 | WIPO | C08H 1/06 |
| WO 95/05162 | 2/1995 | WIPO | A61K 9/00 |

*Primary Examiner*—Margaret W. Glass Moore
*Attorney, Agent, or Firm*—Fish & Richardson P.C.

[57] ABSTRACT

Flowable polymeric microparticulate surgical adhesive formulations are provided which can be activated at the site of the repair to produce a cohesive material with tissue bonding properties to adjacent tissues. The formulation may be activated at the site of repair by mechanical shear forces, heat, ultrasound, UV, or other forms of energy directed at the site.

19 Claims, 1 Drawing Sheet

MICROPARTICULATE SURGICAL ADHESIVE

BACKGROUND OF THE INVENTION

The invention relates to surgical adhesives, and in particular to adhesives which are formed by combination or reaction of their components (hereinafter, "activated") at the wound site.

Surgical adhesives have long been of interest for reconstructing tissues due to the ease of applicability and combined mechanical securement and sealing function. Early use of a fibrin based adhesive, while totally biodegradable, was compromised by poor adhesive strength especially over time as enzyme degradation rapidly depolymerized the fibrin. Modern forms of fibrin adhesives incorporate enzyme inhibitors not only for practical workability, but to retard in-vivo degradation and loss of strength as described in U.S. Pat. No. 4,298,598. Still, these fibrin adhesives require the mixing of two components with long reconstitution times and demonstrate limited and variable working time before setting. In addition, the use of human pooled blood in these products has raised concern regarding potential viral contamination and transmission.

Synthetic adhesive systems, such as the cyanoacrylates and cyanobutylates have high adhesive strength, but have poor degradation properties, with toxic byproducts such as formaldehyde being formed. Further, these materials are mechanically stiff and have poor integration properties with healing tissues. The cyanoacrylate type adhesive systems incorporate almost pure monomer which is initiated by water to form a high strength polymer. The rapidly setting adhesive is difficult to apply in some cases, especially in endoscopic use where the adhesive can set within the catheter lumen. Synthetic prepolymer approaches such as described in U.S. Pat. No. 4,804,691 may utilize biodegradable polymer components, but often rely on toxic components such as isocyanates and metal catalysts. Small amounts of toxicity may have adverse effect on the critical tissue to adhesive interface of a surgical adhesive.

Collagen and gelatin based adhesive solutions have been investigated. Early clinical work with the gelatin-resorcinol-formaldehyde adhesive showed problems with tissue compatibility to the chemical agents and the cumbersome preparation of the adhesive. The use of a more toxicologically compatible collagen solution as described in EPA 0466383A1 requires heating of a collagen solution to partially transform it to gelatin. When applied heated onto the tissues, the material cools to form a bond. In this case the adhesive is only held together by chain entanglement of the collagen/gelatin chains, providing limited mechanical strength which is easily disrupted during subsequent hydration and enzymatic action. Stability of the adhesive material at higher solids content was a performance limitation.

A method described in U.S. Pat. No. 5,156,613 describes the use of a solid collagen filler material which is applied to tissues while an energy source heats both the tissues and the filler material as a tissue welding aid. The denaturation of the tissues and filler, upon cooling provides a mechanical bond. While the approach utilizes high solids content adhesive, essentially a solid, the resultant adhesive material is held together by chain entanglement of the collagen/gelatin chains, limiting mechanical strength and biodegradation resistance. In addition, the inherent damage to underlying tissues of tissue welding approaches in general may prevent use on or near sensitive tissues such as fragile vasculature, nervous tissue, ocular tissue, and areas of cosmetic concern such as the face and neck. A similar approach is described in U.S. Pat. No. 5,209,776 where peptides such as collagen and albumin are mixed with either a polysaccharide or polyalcohol to form a viscous solution which can be used as a sealant or coating. As the coating has no material integrity, it is a weak flowable gel as described, with the primary utility as a adjuvant to tissue welding techniques.

SUMMARY OF THE INVENTION

The present invention describes novel tissue adhesives comprising a flowable polymeric microparticulate formulation which can be site activated to produce a cohesive material with tissue bonding properties to adjacent tissues. When activated, the material can be used to join tissues, seal tissue junctions, act as an injectable embolization agent, augment tissues and reinforce organ walls. The use of microparticulates allows facile applicability as a powder or paste to tissues, with the microparticles able to flow into the tissue crevices and set into the appropriate conformation.

It is an object of the invention to provide a high solids content surgical adhesive which provides total biodegradability, high mechanical integrity, and activation at the delivery site or wound, which alleviates the problem of delay of application after mixing reactive components.

Further objects are to provide a formulation for flowable systems, to prevent damage to contacting tissues during application of the adhesive and biodegradation, to control the degradation rate of the adhesive, and to provide tissue ingrowth features in an adhesive to provide a gradual load transfer to the healing tissues.

DESCRIPTION OF THE PREFERRED EMBODIMENTS

The microparticulate adhesive comprises biodegradable components to allow for natural degradation and progressive incorporation with newly formed tissue. This is particularly important for the clinical success of a surgical adhesive as rapid mechanical failure of the adhesive may lead to clinical problems. Preferred components are biodegradable polymers including biopolymers such as collagen, gelatin, elastin, hyaluronic acid, and fibrin; synthetic degradable polymers such as poly lactic/glycolic acid polymers and copolymers, polyhydroxybuterate, and polycaprolactone; and biological polymerization components such as fibrinogen and factor XIII.

Biopolymers such as collagen and gelatin in particular provide a progressive degradation and load transfer to the healing tissues which would be preferred for clinical efficacy. The tissue integration of the surgical adhesive with the healing tissues may be further promoted by the formation of a porous structure by the microspheres in-situ, thereby allowing tissue ingrowth and mechanical interlocking. Other components, such as growth factors and chemotactic agents, may also be incorporated into the adhesive to further increase tissue incorporation and the performance of the tissue repair.

The use of insoluble microparticles in a solvent mixture greatly reduces viscosity and allows the use of a very high solids content formulation that is flowable. For example, a typical collagen or gelatin composition can achieve solids contents up to approximately 10 to 20 weight % before the viscosity of the polymer increases to form a non-flowable solid. By constraining the polymer into discreet, insoluble microparticles and preventing full polymer mobility, flowable solids contents of approximately 50 weight % can be achieved. Since the solvent vehicle in a polymeric adhesive, such as water, does not participate in forming a structural adhesive, it is important to maximize the amount of structural polymer that is delivered as an adhesive. Small amounts of reactive adhesive components or flow enhancers, may be incorporated into the solvent vehicle for the microparticles, especially if they are of lower molecular weight to prevent viscosity limitations.

Figure 5:
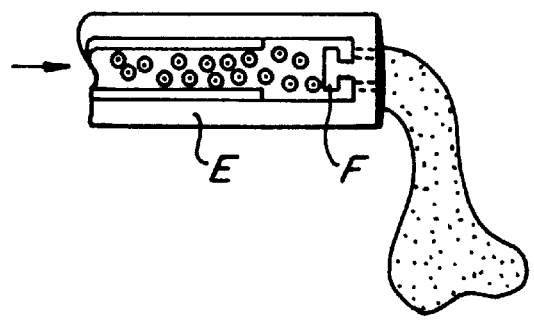
FIG. 5 shows activation of a flowable microcapsule formulation at the tip of a catheter with a rotating outer shaft, E, to spin a rotor, F, in the flow path to mechanically disrupt the microcapsules and deliver an initiated adhesive.

The use of microparticles or microspheres not only allows high solids content, flowable formulations, but also allows activatable components to be packaged within hollow or surface coated constructs similar to industrial one part adhesives. While the typical encapsulation of a catalyst in an industrial one-part adhesive utilizes rigid, fracturable materials such as glass, silica, and rigid thermoplastics to enhance rupture efficiency, these types of materials are not toxicologically acceptable for implantation in tissues. The present invention utilizes microcapsules fabricated entirely from biodegradable polymers that can are rupturable by careful control of capsule thickness, and, optionally, by use of chemical surface stabilization. In one embodiment, hollow microspheres or microcapsules are fabricated from biodegradable materials and packed with reactive components such as synthetic or biological polymerization systems. The reactive components may be isolated in discreet capsules, which polymerize to form an adhesive when the capsules are broken by mechanical shear and mixed, such as at the end of a delivery catheter. An illustration of this method is shown in FIG. 5. An example is the packaging of fibrinogen in microcapsules with separate microcapsules of thrombin. Upon mechanical rupture, the components react to form a fibrin adhesive. Similarly, reactive adhesive components may be packaged within water insoluble capsules and delivered in an non-aqueous solvent to be activated in situ by hydration. Thus, by activation of the adhesive at a catheter tip at the tissue site, working time and pot life considerations are minimized and adhesive kinetics and ultimate properties can be optimized.

Figure 4:
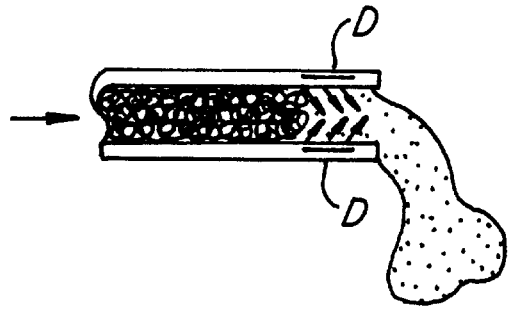
FIG. 4 shows activation of a flowable microparticulate formulation at the tip of a catheter with heat generating elements, D, to deliver a molten polymer adhesive.

Activation methods other than mechanical shear can be utilized with the microcapsules or microparticles. Heat can be used to flow and/or rupture the particles by tailoring the thermal transition properties of the particulate materials. An illustration of that method is shown in FIG. 4. Both biopolymers and biodegradable synthetic polymers have thermal transitions such as the glass transition temperature, which can be tailored for use as adhesive microparticles. Physical methods such as ultrasound can be used in a combined mechanical/thermal activation method. Radio frequency and microwave excitation, while having some patient shielding concerns, may also be utilized to thermally activate or rupture the microparticles to initiate the adhesive.

It is important that the activation of the microparticles trigger reactions which form physiologically stable linkages within the resultant material. Typical linkages used include covalent crosslinks either formed chemically or enzymatically, strong ionic interactions such as chelation, strong hydrophobic interactions, or inter-chain entanglement of polymers. For high physical strength, covalent crosslinking and/or chain entanglement are preferred. In the case of chain entanglement alone, such as the application of a heat activatable thermoplastic polymer component, it is important that the glass transition of the polymer be above physiological temperature to form a stable material. Otherwise, the resultant material would lack material integrity within the body, as occurs with non-crosslinked gelatin, for example, with a transition temperature of about 37° centigrade.

Besides rupturing the microparticles to release adhesive components, the particles themselves may physically participate in the adhesive material. The microparticles or microcapsules are fabricated from high strength degradable polymers with affinity for the adhesive components. In a system where microcapsules are ruptured to mix and initiate a chemical adhesive, the wall components will be incorporated into the final adhesive material, acting as particulate reinforcements, similar to glass filled polymers. The same structural properties which allow the microcapsule to resist premature rupture during use can be further tailored to provide structural reinforcement of the adhesive material, especially controllable by crosslinking the capsule material for the proper biodegradation rate.

In some cases, it may not be necessary or desired to rupture the microparticles. By combining the microparticles with a flowable component which can be set into a solid, or by activating the surface of the microparticles, polymer bridges between particles may be formed to provide structural material from the joined particles, similar to a sintered polymer. Suitable activation methods may be used, such as heat to activate a thermoplastic polymer component or coating of the microparticles. Other particle bridging components include collagen and gelatin, which will flow upon controlled heating and can be further enhanced by a thermoplastic coating or chemical surface graft such as polylactic/glycolic acid polymers. As a bridging component, non-encapsulated polymer or reactive components such as difunctional epoxides reagents may be used to facilitate adhesive setting. Other particle bridging methods include optically activatable groups such as acrylate functional materials which may be incorporated onto the microparticles or formulated as a non-encapsulated component.

When significant portions of microparticles remain at least partially intact, the formation of channels of microparticles occur in the material. Degradable microparticles may be used which to rapidly degrade and form a porous network during biodegradation allowing tissue ingrowth and progressive load transfer to the healing tissues, which is ideal for preventing failure of the surgical adhesive repair.

The degradable microparticles may be fabricated by many available methods. Dry materials can be pulverized and sieved to produce irregular solid particles of selected size range. Irregular particles, while simple to fabricate, tend to pack and clog during flow at high solids contents. Microspheres, with a smooth outer surface have less tendency to interlock with other particles, allowing for increased solids content of a flowable formulation. Microspheres can be fabricated by a variety of method including spray drying, coacervation/emulsion methods, and droplet coagulation. In a preferred method for making hollow microspheres, a limited amount of cross-linking agent can be applied to solid microspheres, then the cross-linking reaction is quenched. The uncrosslinked centers may be extracted with a suitable solvent which swells the cross-linked shell and dissolves the uncrosslinked centers.

Polymers in particular lend themselves to microsphere fabrication. Polymeric microspheres may be further tailored after fabrication by chemical crosslinking to control solubility and biodegradation properties, and also chemically grafted or coated for chemical activation. Microspheres with hollow cavities may be used to isolate reactive adhesive components. Such microcapsules may be formed with single or multiple cavities by methods such as interfacial deposition, spray drying over a removable core, and the like. To package the reactive components, they may be formed into particles and coated during fabrication into microspheres. Alternatively, some reactive components of low molecular weight may be incorporated by swelling the prefabricated microcapsules with a solution of the component and allowing for diffusion into the microcapsule interior.

It is preferred that the biodegradable microparticles have an activatable mechanism to allow in-situ formation of a cohesive material. Heat can be used to fuse the microparticulate surfaces together with the degree controlled by the microparticle surface composition and thermal transition properties. In one method, gelatin particles are fused together to form a cohesive mass upon heating at the end of a catheter tip. The gelatin thermal transition may be altered by the selection of the gelatin molecular weight, degree of deamidation, the type and extent of side chain modifications, and the degree of chemical crosslinking with difunctional chemical agents such as dialdehydes and diisocyanates or peptide crosslinking agents such as carbodiimides. Less crosslinked materials show lower temperatures needed for flowing of the particulates into a cohesive mass. The use of a thermoplastic synthetic polymer such as polylactides/glycolides co-formulated in the adhesive increases strength and provides a multiphased structure to the heat activated adhesive. The physical properties of such polymers may be selected or tailored by molecular weight, copolymer content, and plasticizer content. In one embodiment, thermoplastic degradable polymers such as polylactides, polyglycolides and glycolide/lactide copolymers, and lactone polymers may be coated or covalently grafted to the surface of a protein microsphere, with the resulting microspheres having thermal bonding properties. Additional material stability can be achieved by the use of a heat activatable crosslinking component, such as a difunctional epoxide. Suitable chemical forms include diepoxide functional polyethylene glycols and polypropylene glycols, with activation occurring at temperatures ranging from room temperature to approximately 100 degrees C while demonstrating suitable toxicology.

Figure 1:
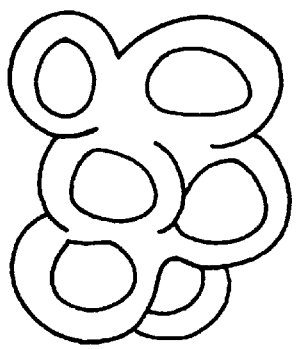
FIG. 1 shows the activation of the surface of microparticles to form a solid material by polymer bridging.

Another method of activation is the use of light initiated polymerization of co-formulated monomers or activatable crosslinkers. In one embodiment, the activatable crosslinkers are chemically grafted to the surface of the biodegradable microparticles to promote high material integrity. Acrylate chemical functionality may be grafted onto gelatin microspheres for light activated polymerization of a particle bridging component such as acrylate and vinyl terminated polymers. An illustration of surface bridged particles is shown in FIG. 1.

Figure 2:
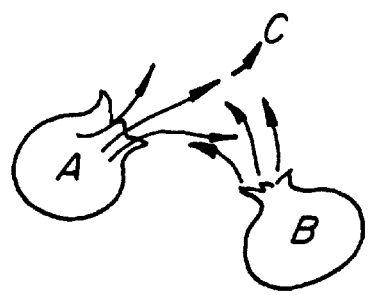
FIG. 2 shows the activation of a polymerization mechanism by the mixing of encapsulated reagents A and B to form a product C.

Another method of activation is the mechanical disruption of hollow microspheres to allow mixing of reactive components. An illustration of such a method is shown in FIG. 2. For a biological adhesive, for example, fibrinogen and factor XIII formulations form a useful surgical adhesive system, although with intensive preparation required and short working time. However, the encapsulation of the fibrinogen in a biodegradable polymer shell and formulation with a factor XIII containing solution provides a formulation readily applied with a catheter incorporating a mechanical disruption/mixing tip. Upon dispensing, there is initiation of the fibrin adhesive to form a cohesive material. Materials having more rapid setting kinetics may be used since working time is short. Typically, a fibrin based adhesive incorporates at least 80 units of factor XIII activity per gram of fibrinogen and small amounts of plasminogen activator inhibitor to aid shelf life and extend working time, and protease inhibitor to increase in-situ residence time. With the encapsulation of either the factor XIII or the fibrinogen monomer, or both, a one component activatable biological adhesive is produced.

Similarly, a combination of a synthetic polymerization initiator and monomer may be sequestered into microencapsulated materials for activation upon mechanical disruption and mixing. Examples include polyethylene glycol, polyethylene glycol/lactide or glycolide copolymers, reacted with polyethylene glycol diisocyanate, or other reactive difunctional agents. Cyanoacrylate monomer may be microencapsulated to prevent the initiation of polymerization by water until delivered at the catheter tip, thereby preventing setting and blockage in the catheter lumen.

Figure 3:
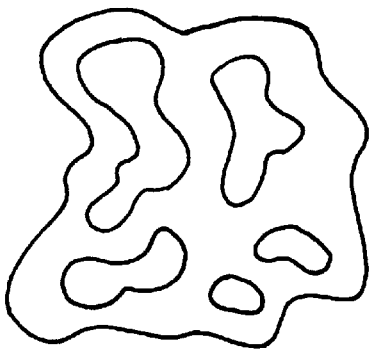
FIG. 3 shows the formation of a material with channels formed by activation of a particulate polymer composition.

Furthermore, rapidly degradable microparticles may be incorporated into the adhesive. Upon degradation of such microparticles channels or pores will be formed which are beneficial for tissue in-growth. An illustration of an adhesive with such channels is shown in FIG. 3.

The activation of the microparticulate adhesive can be performed at the surgical repair site by first dispensing the adhesive and then activating it with either light, heat, radio frequency, or other form of energy. For endoscopic use, a catheter with an activation mechanism at the tip is preferred. A concentric heating element around the catheter tip provides activation that can be coordinated with the feeding of the microparticles to dispense an activated adhesive. Similarly, for reactive adhesive systems where microcapsules are ruptured and mixed, small gear mechanisms, rotating blades, or narrow orifices provide suitable mechanical shear for activation. Small ultrasonic transducers may be incorporated into a catheter, providing both mechanical and thermal energy to both rupture microcapsules and thermally activate the material. Similarly, for optical systems, a fiber optic incorporated into the catheter tip may provide suitable adhesive activation at the dispensing tip.

EXAMPLE 1

Gelatin/Hyaluronic Acid Microcapsules Activated by Heat—Biopolymer microcapsules were prepared containing dyed mineral oil by means of complex coacervation using the sodium salt of hyaluronic acid as the anionic polymer. The ratio of ingredients were as follows:

| | |
|---|---|
| gelatin, type A, 200 bloom | 6 parts by wt |
| hyaluronic acid, sodium salt | 1 part |
| water | 100 parts |
| mineral oil, dyed | 25 parts |

Aqueous dispersions of the polymers were prepared, mixed together and adjusted to pH of 6.75 while heating to 36 degrees C. After emulsification of the mineral oil into the dispersion, the pH was slowly adjusted to 4.80 to stabilize the microcapsules. The resulting oil-containing microcapsules were retrieved by filtration and converted to a free flowing powder by solvent exchange with isopropyl alcohol with subsequent lyophilization.

The dyed mineral oil contained within the microspheres thus serving as an active agent analog, the pre-reactant component consisted of an aqueous slurry prepared at approximately 20% by weight and adjusted to a basic pH. Microscopic examination of the slurry revealed discrete multicore microcapsules uniformly dispersed in a water medium. The slurry was fed to the delivery site by a syringe pump and activated at the tip of the assembly through a heated nozzle. The nozzle consisted of a brass tube spirally wrapped with heater wire, all under a layer of fiberglass insulation. The nozzle temperature was adjusted by a Variac power controller applied to the heater coil. The slurry was pumped at approximately 20 ml/min, and heated to approximately 85 degrees C. Microscopic examination of the resulting material revealed that the microcapsules had ruptured and dissolved, releasing the oil contents from the protective gelatin shell.

EXAMPLE 2

Gelatin/Hyaluronic Acid Microcapsules Activated by Ultrasound—Gelatin microcapsules containing dyed mineral oil as previously described were prepared in accordance with the first example. A 20% aqueous slurry was prepared and adjusted to a basic pH. Using a Heat Systems model 2020XL ultrasonic generator with standard probe and microtip horn, the slurry was sonicated at a setting of 5 for approximately 40 seconds. Microscopic examination of the resulting mixture revealed that the encapsulated oil had been released from the ruptured polymer capsules.

EXAMPLE 3

Thrombin Based Adhesive Utilizing Encapsulated Fibrinogen Activated Mechanically—Fibrinogen microspheres are prepared by coacervation of an aqueous dispersion emulsified into mineral oil. Slow dehydration with the addition of cold isopropyl alcohol yields a fibrinogen microsphere preparation of approximately 50 micron diameter. The resulting particles are isolated by centrifugation and washed in isopropyl alcohol and dried under vacuum. The free flowing particles are then encapsulated with a light coating of polylactic acid by spray drying. The particles are suspended in a methylene chloride dispersion of polylactic acid, in the range of 0.05 to 50 weight percent. The lower concentrations are preferred to form a thin encapsulating shell. The resulting coated microspheres are then formulated into a 30 weight percent slurry with phosphate buffer with thrombin or Factor XIII activity in the ratio of approximately 100 to 1000 units of Factor XIII activity per gram of encapsulated fibrinogen. Upon passage of the flowable slurry through a catheter with a mechanical shearing tip, the fibrinogen is released and forms a cohesive gel-like material upon reaction with the thrombin.

EXAMPLE 4

Gelatin Particulate Based Adhesive Formulation Activated by Heat—A flowable gelatin slurry was prepared by first mixing polyethylene glycol 400, glycerol, and water in the following proportions:

| | |
|---|---|
| polyethylene glycol 400 | 0.75 grams |
| glycerol | 2.25 grams |
| water | 1.00 grams |

To this solution was added 3 grams of gelatin powder having a grain size no greater than approximately 500 microns to form a 40 weight percent solids slurry. The slurry was fed to the delivery site using the nozzle system described in the first example. The slurry was pumped at approximately 3 ml/min and heated to approximately 100 degrees C. Exiting the nozzle was a highly viscous, molten gelatin. Upon cooling the material hardened into a cohesive rubbery mass.

EXAMPLE 5

Gelatin Microsphere Based Adhesive Formulation with In-Situ Crosslinking—A gelatin adhesive formulation was prepared with the following components:

| | |
|---|---|
| gelatin microspheres, ~25 to 50 micron diameter | 250 mg |
| polyethylene glycol, dialdehyde, 3400 MW | 50 mg |
| deionized water | 2 grams |

The mixture was quickly mixed and allowed to set at room temperature. After one half hour, the material has become a firm gel. Incubation at 45 degrees C showed a stable gel, unlike the non-crosslinked control sample which dissolved. Microscopic examination showed a cohesive mass of microspheres, bridged together to form the material.

EXAMPLE 6

Gelatin Particulate Based Adhesive Formulation with Heat Activated Crosslinking—A gelatin adhesive formulation was prepared with the following components:

| | |
|---|---|
| gelatin powder, grain size <500 microns | 9 grams |
| polyethylene glycol 400 | 2.25 grams |
| glycerol | 7.5 grams |
| polyethylene glycol, diepoxide, MW3400 | 200 mg |

The components were stirred together to form a particulate slurry of approximately 47 weight % solids. With a syringe, the mixture was extruded through a heating element with a 0.5 cm bore, heated to approximately 140 degrees C. The extrudate was a uniform transparent amber color, indicating fusion of the gelatin material. Once cooled, the material exhibited a cohesive, rubbery properties. The material was stable when placed in water heated to 40 degrees C for 17 hours, indicating crosslinking into a stable adhesive material.

EXAMPLE 7

Hollow Gelatin Microsphere with Thermoplastic Polymer Graft Based Adhesive Formulation, Activated by Heat—Hollow gelatin microspheres were prepared by fabricating ~50 micron diameter gelatin microspheres by emulsion of a 200 bloom gelatin dispersion into mineral oil. The microspheres were recovered after precipitation with cold isopropanol and surface crosslinked in a mixture of 1,3 dimethylaminopropyl-3-ethylcarbodiimide hydrochloride at 0.67 mg/ml in 1:14 volume ratio of water:acetone for 12 minutes at room temperature. The microsphere crosslinking was quenched with a chilled, acidified water:acetone solution, and washed two time by centrifugation in acetone.

The microspheres were resuspended in deionized water and heated to 80 degrees C for 4 hours, after which the microspheres were isolated by centrifugation. Approximately 21% of the original gelatin weight was remaining, indicating an extraction of the uncrosslinked center. The resulting microspheres demonstrated a hollow morphology with very thin walls when examined microscopically. The gelatin microspheres were then washed in THF and grafted with caprolactone to form a thermoplastic polycaprolactone coating, covalently attached to the microsphere surface. Approximately 50 mg of the dried microspheres were placed in a reaction mixture containing the following components:

| | |
|---|---|
| 0.2 ml | triethyl aluminum, 50% in toluene |
| 2.0 grams | caprolactone monomer |
| 8.0 grams | tetrahydrofurane |

The reaction was heated for approximately 5 hours at 40 degrees C. The microspheres were isolated from the reaction mixture by centrifugation at 2400 rpm for 15 minutes. The microspheres were washed 3 times in fresh THF solvent and recovered as dry, free flowing particles. When heated on a glass slide at approximately 90 degrees C, the particles fused into a mass of aggregated microspheres. Under microscopy, the fused mass of material showed a reticulated morphology.

EXAMPLE 8

Gelatin Particulate Based Adhesive with Thermoplastic Binding Agent—A polymer dispersion of polycaprolactone (Solvay CAPA 650), 7.2 g in 30 ml of methylene chloride was prepared. A separate dispersion of gelatin, 4.8 g of gelatin was dissolved with light heating into 11.2 ml of deionized water containing 1.6 g each of glycerol and PEG 400. A finely divided emulsion was formed by mixing the two immiscible solutions together with vigorous mixing. The viscous mixture was then poured on a glass plate, heated to 80 degrees C on a glass plate and allowed to dry at room temperature overnight. The material was then heated to 80 degrees C to form a melt, and molded into cylindrical shapes approximately 8.5 cm long and 0.65 cm in diameter. The resulting flexible rod was then melted and extruded through a heating tube of 0.2 cm diameter and heated to approximately 140 degrees centigrade. A molten polymer was dispensed which cooled into a very cohesive, flexible material with an appearance similar to the starting material. A 0.134 g specimen of the dispensed adhesive was placed in deionized water at 40 degrees C for approximately 64 hours to simulate extraction of the gelatin particle component in-vivo. The specimen was then removed and allowed to dry. The weight of the specimen was 0.064 g, a reduction of approximately one half of the weight, which roughly corresponds to the gelatin and glycerol/PEG components. The specimen had become white, the color of the caprolactone polymer. Microscopic inspection of the sample showed that the gelatin had been dissolved to form a surface porosity, with both interconnected and non-interconnected pores through the material cross-section.

What is claimed is:

1. A microparticulate surgical adhesive composition comprising biodegradable polymeric microparticles having an impermeable outer shell, which are activatable in-situ by rupturing said impermeable outer shell to form a high strength, cohesive material which is physiologically stable.

2. An adhesive composition according to claim 1 which is activatable in-situ by rupture and fusion of said microparticles to form said cohesive material.

3. An adhesive composition according to claim 1 which is activatable in-situ to form said cohesive material which comprise channels or pores for tissue integration.

4. An adhesive composition according to claim 1 comprising a flowable slurry with a physiologically compatible solvent.

5. An adhesive composition according to claim 1 which is activatable by heat.

6. An adhesive composition according to claim 1 which is activatable by ultrasound energy.

7. An adhesive composition according to claim 1 which is activatable by radio frequency or microwave energy.

8. An adhesive composition according to claim 1 which is activatable by light.

9. An adhesive composition according to claim 1 which is activatable by mechanical shear.

10. An adhesive composition according to claim 1 which further comprises a particle bridging component.

11. An adhesive composition according to claim 1 which further comprises a coating or chemical graft on the surfaces of said microparticles.

12. An adhesive composition according to claim 1 which further comprises growth factors or chemotactic factors.

13. An adhesive composition according to claim 1 which further comprises wound healing agents, anti-infective agents or anti-inflammatory agents.

14. An adhesive composition according to claim 1 which further comprises hollow microparticles.

15. An adhesive composition according to claim 1 which further comprises coated components which are ruptured to initiate formation of adhesive.

16. An adhesive composition according to claim 1 which further comprises collagen or gelatin microparticles.

17. An adhesive composition according to claim 1 which comprises fibrinogen and factor XIII.

18. An adhesive composition according to claim 1 which comprises a biodegradable thermoplastic polymer.

19. A flowable adhesive composition according to claim 1 having a solids content greater than 20 weight percent.

* * * * *